United States Patent [19]

Maeda et al.

[11] Patent Number: 5,700,397
[45] Date of Patent: Dec. 23, 1997

[54] EMULSIFIER, EMULSION COMPOSITION, AND POWDER COMPOSITION

[75] Inventors: Hirokazu Maeda; Hitoshi Furuta; Taro Takahashi; Chiemi Takei; Hiroko Kurita, all of Kitasoma-gun; Yoko Sato, Tsukuba-gun, all of Japan

[73] Assignee: Fuji Oil Co., Ltd., Osaka, Japan

[21] Appl. No.: 193,105

[22] PCT Filed: Jun. 14, 1993

[86] PCT No.: PCT/JP93/00793

§ 371 Date: Feb. 9, 1994

§ 102(e) Date: Feb. 9, 1994

[87] PCT Pub. No.: WO93/25302

PCT Pub. Date: Dec. 23, 1993

[30] Foreign Application Priority Data

| Jun. 16, 1992 | [JP] | Japan | 4-221879 |
| Jun. 16, 1992 | [JP] | Japan | 4-221880 |
| Nov. 20, 1992 | [JP] | Japan | 4-335267 |

[51] Int. Cl.$^6$ .................. B01J 13/00; A23L 1/035; B01F 17/00
[52] U.S. Cl. .............. 252/312; 426/654; 427/213.3; 428/402.24; 521/65
[58] Field of Search .............. 252/312; 424/278.1; 426/654; 427/213.3; 428/402.24; 521/65

[56] References Cited

FOREIGN PATENT DOCUMENTS

| 0 470 872 | 2/1992 | European Pat. Off. |
| 0 521 707 | 1/1993 | European Pat. Off. |
| 60-146828 | 8/1985 | Japan |
| 64-62303 | 3/1989 | Japan |
| 2-276801 | 11/1990 | Japan |
| 3-58758 | 3/1991 | Japan |
| 3-37904 | 6/1991 | Japan |
| 3-502407 | 6/1991 | Japan |
| 3-280858 | 12/1991 | Japan |
| 3-290157 | 12/1991 | Japan |
| 156725 | 7/1922 | United Kingdom |
| 173230 | 10/1922 | United Kingdom |
| 1062423 | 3/1967 | United Kingdom |

OTHER PUBLICATIONS

"Polysaccharides of Soybean Seeds—Part I—Polysaccharide Constituents of 'Hot–Water–Extract' Fraction of Soybean Seeds and an Arabinogalactan as its Major Component," Morita, Makio, *Agr. Biol. Chem.*, vol. 29, No. 6, pp. 564–573, 1965.

"Polysaccharides of Soybean Seeds—Part II—A Methylated Arabinogalactan Isolated from Methylated Product of 'Hot–Water–Extract' Fraction of Soybean Seed Polysaccharides," Morita, Makio, *Agr. Biol. Chem.*, vol. 29, No. 7, pp. 626–630, 1965.

"Polysaccharides of Soybean Seeds—Part III—1,4–Linked Galacto–di– and Trisaccharides from Partial Acid Hydrolysate of the 'Hot–Water–Extract' Fraction of Soybean Seed Polysaccharides," Morita, Makio, et al., *Agr. Biol. Chem.*, vol. 31, No. 3, pp. 314–318, 1967.

"Rheological Behavior of Soluble Polysaccharide Fractions from Soybeans," Thompson, D. B., et al., *Food Hydrocolloids*, vol. 1, No. 4, pp. 333–337, 1987.

"Non–Starch Polysaccharides of Seeds of Soybean," Ravindran, G., *J. Natn. Sci. Coun. Sri Lanka*, vol. 16, No. 2, pp. 223–228, 1988.

*Primary Examiner*—Shean C. Wu
*Attorney, Agent, or Firm*—Wallenstein & Wagner, Ltd.

[57] ABSTRACT

An emulsifier comprising as an active ingredient a water-soluble hemicellulose derived from a soybean cotyledon, an emulsion composition comprising the emulsifier, and a powder composition produced by powdering the emulsion composition. The emulsifier of the present invention can provide a very stable emulsion composition.

8 Claims, No Drawings he present invention relates to an emulsifier having good
EMULSIFIER, EMULSION COMPOSITION, AND POWDER COMPOSITION This application is a 371 of PCT/JP93/00793, filed Jun. 14, 1993.

TECHNICAL FIELD

The present invention relates to an emulsifier having good emulsifying and emulsion-stabilizing properties, an emulsion composition containing the same, and a powder composition produced by powdering the emulsion composition.

BACKGROUND ART

In general, emulsifiers are roughly classified into monomolecular emulsifiers and polymer emulsifiers. The monomolecular emulsifiers are the so-called "surfactants" and include fatty acid soaps, glycerin esters, and sugar esters. These emulsifiers are used in the form of a proper mixture of two or more of them depending upon application to produce various emulsion compositions, for example, emulsion flavors, dressings, and creams such as coffee creams. In general, however, these monomolecular emulsifiers had problems such as a high susceptibility to a change in pH and loss of the emulsifying property by addition of salts and a change in concentration attributable to dilution.

The polymer emulsifiers include gums including gum arabic, naturally occurring emulsifiers such as casein, and synthetic emulsifiers such as salts of acrylic acid and polyvinyl alcohol. These polymer emulsifiers are used in the production of emulsion compositions such as emulsion flavors or powder compositions such as powder fats and oils and powder flavors. The powder composition is produced by emulsifying an oil, a lipophilic flavor or the like, and an aqueous component with a polymer emulsifier and then subjecting the emulsion to spray drying or the like. In this case, the powder composition is often in the form of a microcapsule.

Gum arabic, dextrin, chemically modified starch, etc. are generally used as the polymer emulsifier. In particular, gum arabic is used widely in the field of powder compositions, such as powder fats and oils and powder flavors, by virtue of its excellent emulsifying property and film-forming property. Gum arabic is produced by refining exudates of trees, dextrin is produced by reducing the molecular weight of starch, and chemically modified starch is a starch derivative produced by chemically modifying starch.

There are various microencapsulation methods. Among them, the complex coacervation method is the method most commonly used in industry and utilized in microencapsulation in the field of pressure-sensitive copying paper including noncarbon paper, agricultural chemicals, pharmaceuticals, etc. The complex coacervation method is a technique where two dilute aqueous solutions, i.e., a dilute aqueous solution of a polycation colloid and a dilute aqueous solution of a polyanion colloid, are mixed with each other to cause a phase separation into a colloid-rich phase and a colloid-lean phase by electrical interaction. The colloid-rich phase is utilized as a film for encapsulation.

Examples of the polycation colloid used in the complex coacervation method include proteins such as gelatin, gelatin derivatives, albumin, casein, hemoglobin, and soluble collagen. On the other hand, examples of the polyanion colloid include gum arabic, sodium alginate, carageenan, tragacanth gum, carboxymethyl cellulose, agar, polyvinylbenzenesulfonic acid, polyvinyl methyl ether/maleic anhydride copolymers and surfactants.

Naturally occurring substances which are polymer emulsifiers and serve as polyanion colloids, such as gum arabic, have the following large problems. Specifically, in order to provide a stable emulsion, it is necessary for them to be used in a high concentration. Further, the supply thereof is susceptible to weather of production countries, so that the price fluctuation is large. Further, the variation in quality is also high. For this reason, in recent years, naturally occurring polymer emulsifiers which can be stably supplied have been desired in the art. It is noted that synthetic polymer emulsifiers, such as polyacrylates and polyvinyl alcohol, are used in limited applications because they have problems of emulsifying property and the like. On the other hand, dextrin and chemically modified starch can be stably supplied. However, when they are used, the film stability of the coating compound is inferior to that in the case where use is made of gum arabic. Further, the emulsifying property of dextrin is so low that other suitable emulsifiers should be used in the production of powder fats and oils and powder flavors.

As described above, in the emulsifiers used in various applications, the emulsions should remain stable for a long period of time, and when they are utilized in foods, it is necessary to provide a feeling of satisfaction from eating. For example, gum arabic is extensively used as the emulsifier for emulsion flavors. It, however, has the following drawbacks. In order to attain the above-described stable emulsion, use in a high concentration is necessary. Further, the supply is susceptible to the weather of production countries, so that the price fluctuation is large. Further, the variation in quality is great. Xanthan gum or the like is widely used as the emulsifier for dressings. Xanthan gum renders the dressings very viscous, however. Such dressings do not provide a feeling of satisfaction from eating. Further, casein is used for creams such as creams for coffee. Casein, however, is not always satisfactory because it is highly susceptible to a change in pH and the emulsion is broken upon dilution. Polymer emulsifiers used for powder fats and oils and powder flavors are required to be stably supplied and excellent in not only emulsifying property in the production of emulsions but also the stability of the coated compound and the strength of the coating film. At the present time, however, there is no emulsifier capable of simultaneously satisfying all the above requirements.

The polycation colloids and the polyanion colloids for the complex coacervation may be used in any combination of the above-described compounds. The best combination is a combination of gelatin from the former compounds with gum arabic from the latter compounds. This combination is widely used in the art. However, abnormal weather in recent years gave rise to an ever-increasing tendency to a reduction in the production of gum arabic. For this reason, the development of polyanion colloids as an alternative to gum arabic, which can be stably supplied, has become strongly desired in the art.

DISCLOSURE OF THE INVENTION

Under the above-described circumstances, the present inventors have made extensive and intensive studies and, as a result, have found that, by using as an emulsifier a water-soluble hemicellulose obtained by extraction from a soybean cotyledon, an emulsion composition having good emulsification property, storage stability, pH resistance, salt resistance, and temperature resistance can be provided, a good complex coacervation can be provided particularly when the water-soluble hemicellulose is used in combination with a polycation colloid such as gelatin, spray drying of such an emulsion composition can provide a stable powder composition having an excellent film strength, and drying of the complex coacervation can provide a very good microcapsule. The present invention has been completed based on such findings.

Therefore, according to the present invention, there is provided an emulsifier comprising as an active ingredient a water-soluble hemicellulose derived from a soybean cotyledon, an emulsion composition comprising the emulsifier, and a powder composition produced by powdering the emulsion composition.

BEST MODE FOR CARRYING OUT THE INVENTION

The average molecular weight of the water-soluble hemicellulose provided by extraction from soybean cotyledon is preferably in the range of from several thousands to several millions, particularly preferably in the range of from 5000 to one million. When it is excessively high, the water-soluble hemicellulose becomes excessively viscous, so that the emulsification becomes difficult. The average molecular weight of the water-soluble hemicellulose is a value determined by the limiting viscosity method wherein the viscosity is measured in a 0.1M $NANO_3$ solution using a standard pullulan (manufacturedby Showa Denko K.K.) The uronic acid content was measured by the Blumenkrantz method, and the neutral sugar content was measured by the GLC method after alditol acetation.

The water-soluble hemicellulose useful in the present invention is extracted from the soybean cotyledon. In this case, okara (bean-curd refuse) produced as a by-product in the production of bean curd, soybean milk, or separated soybean protein may be used as the raw material.

A preferred example of the process for producing the water-soluble hemicellulose will now be described. Specifically, the above-described raw material is heat-degradation in an acidic region, preferably in a pH region around the isoelectric point of each protein, preferably at 80° C. to 130° C., still preferably 100° C. to 130° C. When the heat degradation temperature exceeds 130° C., since the content of low-molecular saccharides including monosaccharides is increased, the coloration becomes significant and the emulsification capability are unfavorably lowered. On the other hand, when the heat degradation temperature is below 80° C., the amount of extraction unfavorably becomes very low. Then, a water-soluble fraction may be fractionated and then dried as it is or alternatively subjected to, for example, an activated carbon treatment, a resin adsorption treatment, or an ethanol precipitation treatment to remove hydrophobic substances or low-molecular substances and dried to provide a water-soluble hemicellulose.

For example, when the water-soluble hemicellulose solution is in the form of a 10% aqueous solution, the viscosity is preferably 200 cP or less, still preferably 100 cP or less, further preferably 50 cP or less. When the viscosity of the water-soluble hemicellulose solution is excessively high, in some cases, no good emulsion can be provided. For this reason, when the water-soluble hemicellulose has a high-molecular weight and an excessively high viscosity, it is generally effective to perform treatment for further reducing the molecular weight prior to decoloration, deodorization, and drying. The treatment for reducing the molecular weight can be effected by enhancing conditions for the heat degradation. Alternatively, it is also possible to use a technique where a degraded extract of the hemicellulose is treated with an alkali, an acid, heat, an enzyme, or the like.

When the water-soluble hemicellulose is used as an emulsifier for emulsion flavors, it becomes possible to provide an emulsion composition superior to that provided by using gum arabic or chemically modified starch in an emulsified state, stability such as storage stability, pH resistance, salt resistance, temperature resistance, and alcohol resistance, and suspension stability. When this water-soluble hemicellulose is used in dressings, the resultant dressings have a considerably lower viscosity and a plainer taste as compared with those provided by using xanthan gum or starch. Further, when the water-soluble hemicellulose is used in creams, such as whiteners for coffee, the resultant creams are less likely to cause breaking of emulsion even when they are subjected to a change in pH or diluted.

The water-soluble hemicellulose can be widely applied to applications besides foods, for example, cosmetics and creams for pharmaceuticals, such as hand creams and ointments. Further, it is also possible to utilize the water-soluble hemicellulose in emulsion compositions used in all bioindustrial applications, for example, agricultural chemicals, such as insecticides and herbicides in an oil-in-water type emulsion form, or assistants for printing. In this case, in the resultant products, the emulsion remains stable for a long period of time and, further, reins stable even after application and exhibit excellent persistence of potency.

In the present invention, although the water-soluble hemicellulose can be used alone as an emulsifier, the combined use of the water-soluble hemicellulose and conventional emulsifiers often contributes to a further improvement in the effect and can compensate for drawbacks of various conventional emulsifiers. Examples of conventional monomolecular emulsifiers usable in combination with the water-soluble hemicellulose include various anionic surfactants including fatty acid soaps, cationic surfactants, such as quaternary ammonium salts, nonionic surfactants, such as glycerin fatty acid esters and sugar esters, and amphoteric surfactants, such as lecithin. On the other hand, examples of conventional polymer emulsifiers usable in combination with the water-soluble hemicellulose include naturally occurring emulsifiers, for example, glue plants (funori), agar, carageenan, furcellaran, tamarind seed polysaccharides, gum tare, gum karaya, pectin, xanthan gum, sodium alginate, tragacanth gum, guar gum, locust bean gum, pullulan, jellan gum, gum arabic, gelatin, albumin such as whey, casein sodium and various starches. Semisynthetic glues include carboxymethyl cellulose (CMC), methyl cellulose (MC), hydroxyethyl cellulose (HEC), alginic acid propylene glycol ester, chemically modified starches including soluble starches, and synthetic glues including polyvinyl alcohol and sodium polyacrylate.

In some cases, the addition of succharides including sucrose and starch syrup, polyhydric alcohols, such as glycerin, D-sorbitol, and propylene glycol, for example, and acidulants, such as lactic acid, vinegar, citric acid, and malic acid, to the water phase contributes to an improvement in the stability of the emulsion. It is also possible to utilize fading preventives, preservatives, and other additives, such as L-ascorbic acid or its derivatives and aminocarbonylation products.

The oil phase used in the emulsion composition of the present invention may comprise any oleaginous substance that is virtually insoluble in water, and examples thereof include conventional fats and oils, oil-soluble flavors, oil-soluble pigments, wax, insecticides, herbicides, oil-soluble pharmaceuticals, and oil-soluble reagents. If a long-term suspension stability is necessary also when the emulsion is used after dilution as in emulsion flavors, use of a specific gravity modifier having a specific gravity of 1 or more is preferred for the purpose of increasing the specific gravity. Examples of the specific gravity modifier include brominated oils, sugar esters, such as sucrose acetic acid isobutyric acid ester (SAIB), dammar, rosin, and ester gum. Therefore, the present invention can be utilized widely in all bioindustrial applications including foods such as emulsion flavors, dressings, and creams, cosmetics such as hand creams, pharmaceuticals such as ointments, agricultural chemicals such as insecticides, and printing assistants.

Further, use of the above-described water-soluble hemicellulose as a polyanion colloid in the complex coacervation process can provide an excellent coacervate as in the use of gum arabic.

When the water-soluble hemicellulose derived from a soybean cotyledon useful in the present invention is used alone as a base for powdering, it is excellent in emulsification property, film-forming property, and film strength, which renders the stability of the coated fats and oils and flavors con,parable favorably with that in the case where gum arabic is used as a base for powdering. Therefore, since the emulsifier according to the present invention serves also as a base for powdering, the present invention include the use of the emulsifier as a base for powdering.

In the present invention, although the water-soluble hemicellulose can be used alone as a polyanion colloid, the combined use of the water-soluble hemicellulose and conventional polyanion colloids can often compensate for drawbacks of the polyanion colloids. As described above, examples of the conventional polyanion colloid include gum arabic, sodium alginate, carageenan, tragacanth gum, carboxymethyl cellulose, agar, polyvinylbenzenesulfonic acid, polyvinyl methyl ether/maleic acid copolymer, and surfactants.

A method for producing a complex coacervation using gelatin and a water-soluble hemicellulose will now be described. In the combined use of the gelatin and the water-soluble hemicellulose, the weight ratio of the gelatin to the water-soluble hemicellulose is in the range of from 10:1 to 1:10, preferably in the range of from 2:1 to 1:2. Further, in order to form a coacervate, it is necessary for the concentration of the gelatin and the water-soluble hemicellulose to be below a certain value, and the concentration of a mixture of both the colloids is preferably 10% or less, preferably 4% or less. However, it is also possible to use a technique where a core substance for the microcapsule is previously dispersed or emulsified in a colloid-rich solution and then diluted to a predetermined concentration to form a coacervate.

When the above-described mixed colloidal solution comprising gelatin and a water-soluble hemicellulose is acidified gradually to a pH value below the isoelectric point of the gelatin while maintaining the temperature above the gelation point of the gelatin, a coacervate is formed. When the temperature of the solution is lowered below the gelation point of the gelatin, a coated microcapsule is formed. Any inorganic acids and organic acids may be used for the acidification so far as they are soluble in water. Even when use is made of any acid, the coacervation can be successfully formed by gradually adding the acid in the form of a dilute solution.

The microcapsule thus obtained is in a water-soluble colloid form and, as such, can be used in an aqueous system. However, in order to bring it to fixed particles, it is necessary to effect a curing treatment using a curing agent. Examples of the curing agent include aldehydes such as formaldehyde, glutaraldehyde, mucochloric acid, glyoxal, glycerin aldehyde, and acrolein, diketones such as o-benzoquinone, p-benzoquinone, and cyclohexan-1,2-dione, tannic acid, gallic acid, and ferric salt. Among them, formaldehyde and glutaraldehyde are particularly preferred. The time necessary for curing may be properly selected depending upon the elution rate of desired core substances.

It is also possible to doubly coat the resultant microcapsule with another coating agent for the purpose of reinforcing the wall of the microcapsule and preventing the occurrence of pinholes. The double coating can be achieved by dissolving a coating material in a microcapsule suspension before or after curing and changing the liquid property or insolubilizing the coating material by adding other materials. Examples of the coating material include compounds soluble in water in an acidic form and insoluble in water in a neutral or alkaline form, for example, cellulose derivatives such as benzylaminomethyl cellulose and diethylaminomethyl cellulose, polyvinyl derivatives such as a vinyldiethylamine/vinyl acetate copolymer, polyvinyl acetal diethylaminoacetate and polydiethylaminomethylstyrene, compounds soluble in water in an alkaline form and insoluble in water in a neutral or acidic form, for example, cellulose derivatives such as cellulose acetate phthalate and cellulose acetate succinate and polyvinyl derivatives such as polyvinyl alcohol phthalate and polyvinyl acetate phthalate, compounds capable of forming insoluble salts such as sodium alginate and carboxymethyl cellulose, and resin base materials wherein polycondensation is involved in an early stage, such as methylol compounds.

The core material used in the microcapsule of the present invention may be any material so far as it is oleaginous or solid and is virtually insoluble in water. Examples thereof include general fats and oils and oil-soluble flavors, or oil-soluble dyes, wax, insecticides, herbicides, oil-soluble pharmaceuticals, oil-soluble reagents, starch powder, silica gel and glass beads. Therefore, the present invention can be utilized widely in all bioindustrial applications, for example, foods such as edible flavors, dressings, and creams, artificial feeds such as feeds for pisciculture, industrial products such as pressure-sensitive copying paper and printing flavors, cosmetics such as hand creams, toiletries such as aromatics, pharmaceuticals such as sustained release pharmaceuticals, agricultural chemicals such as insecticides, and fertilizers.

Further, in the present invention, the coacervation, as such, can be used for drinking purposes.

Embodiments of the present invention will now be described with reference to the following examples, that are for illustrative purposes only and do not limit the spirit and scope of the present invention. In the examples, "parts" and "%" are by weight.

Preparation of Soybean Hemicellulose

To raw okara obtained in an isolation soybean protein production process was added water in an amount of twice the amount of the raw okara. The mixture was adjusted to pH 4.5 with hydrochloric acid and hydrolyzed at 120° C. for 1.5 hr. The reaction mixture was cooled and centrifuged (10000 G×30 min) to separate it into a supernatant and a precipitate. The separated precipitate was further washed with an equal weight of water and centrifuged, and the resultant supernatant was combined with the above supernatant, applied to an activated carbon column, and dried to provide a water-soluble hemicellulose (i).

The water-soluble hemicellulose was dissolved in 0.5% saline, and reprecipitation was repeated three times in such a manner that the ethanol concentration became 50%, followed by desalting with an ion-exchange resin ("Amberlite IR-120 B" manufacturedby Organo Corp.) to provide a water-soluble hemicellulose (ii).

Separately, a water-soluble hemicellulose (iii) was provided in the same manner as that described above, except that the treatment using an activated carbon column was not effected.

The results are summarized as follows.

| | Composition (%) | | |
|---|---|---|---|
| Components | (i) | (ii) | (iii) |
| Water | 5.71 | 7.75 | 5.10 |
| Crude protein | 1.93 | 1.03 | 5.43 |
| Crude ash | 5.29 | 0.22 | 5.30 |
| Polysaccharides | 87.07 | 91.00 | 84.17 |
| Average molecular weight | 178,000 | 207,000 | 114,000 |

Then, the saccharide composition of the water-soluble hemicelluloses (i), (ii), and (iii) was analyzed by the following method. Uronic acid was measured by the Blumenkrantz method, and neutral saccharides were measured by the alditol acetate method using GLC. The results were as follows.

| | Composition of Saccharides (wt. %) | | |
|---|---|---|---|
| Kind of saccharides | (i) | (ii) | (iii) |
| Uronic acid | 20.4 | 16.9 | 19.4 |
| Rhamnose | 1.6 | 2.7 | 2.1 |
| Fucose | 2.7 | 5.2 | 3.9 |
| Arabinose | 19.9 | 19.2 | 23.1 |
| Xylose | 6.4 | 8.4 | 5.8 |
| Galactose | 47.3 | 46.8 | 43.4 |
| Glucose | 1.8 | 0.9 | 2.3 |

EXAMPLE 1

10 parts of the water-soluble soybean hemicellulose (i) was dissolved in 80 parts of water, and a mixed oil comprising 6.5 parts of SAIB (sucrose acetic isobutyric ester) and 3.5 parts of an orange oil was dispersed in the solution to bring the volume of the solution to 100 parts. The dispersion was adjusted to pH 4.0 with a 50% citric acid solution and then emulsified with a homogenizer (300 kgf/cm$^2$). The emulsified product maintained a stable state of emulsion without addition of other emulsifiers and was stable even after cold storage for 3 months.

Then, 120 parts of granulated sugar and 2 parts of citric acid were dissolved in 880 parts of water, and 1 part of the above-described emulsified product was added thereto to provide an orange-like soft drink. This drink was very stable even after the elapse of 3 months.

EXAMPLE 2

An emulsion flavor was prepared on an experimental basis in the same manner as that of Example 1, except that the water-soluble hemicellulose (ii) was used instead of the water-soluble soybean hemicellulose (i). As a result, the emulsion stability was good. Further, an orange-like soft drink prepared using this flavor also had a good stability.

EXAMPLE 3

An emulsion flavor was prepared on an experimental basis in the same manner as that of Example 1, except that the water-soluble hemicellulose (iii) was used instead of the water-soluble soybean hemicellulose (i). As a result, the emulsion stability was good. Further, an orange-like soft drink prepared using this flavor also had a good stability.

Comparative Example 1

An emulsion flavor was prepared on an experimental basis in the same manner as that of Example 1, except that gum arabic was used instead of the water-soluble soybean hemicellulose (i). As a result, separation was observed within one month after the initiation of storage.

Comparative Example 2

An emulsion flavor was prepared in the same manner as that of Example 1, except that a chemically modified starch (Puritygum manufactured by Oji-National Co., Ltd.) was used instead of the water-soluble soybean hemicellulose (i). As a result, separation, precipitation, and gelation were observed within one month after the initiation of storage.

Comparative Example 3

An attempt was made to provide an emulsion flavor in the same manner as that of Example 1, except that arabinogalactan derived from tamarack (manufactured by Mitsubishi Rayon Co., Ltd.) was used instead of the water-soluble soybean hemicellulose (i). However, two-phase separation occurred immediately, so that emulsification cannot be attained.

Comparative Example 4

900 parts of water was added to 100 parts of a commercially available fiber ("Cellfer" manufactured by Nippon Shokuhin Kako Co., Ltd.) which was a fiber prepared by removing starch, protein, lipid, etc. from a husk of corn. The mixture was subjected to autoclaving (140° C., 60 min), heat extraction, and centrifugation (5000 G, 10 min) to obtain a supernatant. Ethanol was added to the supernatant to an ethanol concentration of 60%. Centrifugation (5000 G, 10 min) was effected to collect a precipitate that was then dried to provide a water-soluble corn hemicellulose.

The water-soluble corn hemicellulose was analyzed in the same manner as that of Example 1. The results were as follows.

| Composition (%) | |
|---|---|
| Water | 8.70 |
| Crude protein | 0.36 |
| Crude ash | 1.12 |
| Polysaccharides | 89.82 |
| Average molecular weight | 178,000 |

| Composition of Saccharides (wt. %) | |
|---|---|
| Uronic acid | 4.9 |
| Arabinose | 35.9 |
| Xylose | 45.7 |
| Galactose | 6.1 |
| Glucose | 7.4 |

An emulsion flavor was prepared in the same manner as that of Example 1, except that the above-described water-soluble corn hemicellulose was used instead of the water-soluble soybean hemicellulose (i). As a result, not only was the particle diameter of the emulsion large but also the suspension stability was poor.

The emulsion flavors and orange-like soft drinks prepared in the above examples and comparative examples were stored at 5° C. for 90 days, and the state of emulsion was observed. The results are given in the following table in comparison with one another.

| Ex. and Comp. Ex. | Emulsion flavor | | Orange-like soft drink | |
|---|---|---|---|---|
| | State of Emulsion | Average particle diameter (μm) | State of Emulsion | Odor |
| Ex. 1 | ⊚ | 0.7 | ⊚ | ○ |
| Ex. 2 | ⊚ | 0.8 | ○ | ⊚ |
| Ex. 3 | ⊚ | 0.7 | ⊚ | ○ |
| Comp. Ex. 1 | Δ | 2.3 | ⊚ | ○ |
| Comp. Ex. 2 | X | 10.0 | Δ | ○ |
| Comp. Ex. 3 | X | — | X | X |
| Comp. Ex. 4 | X | 7.2 | X | X |

⊚: very good, v: good, Δ: somewhat poor, X: poor
Note)
The average particle diameter was measured with a laser diffraction particle size distribution measuring device (LA-500 manufactured by Horiba Ltd.).

As is apparent from the above table, when use was made of water-soluble soybean hemicelluloses, the resultant emulsion flavors had a good stability and were stable also when used in drinks.

EXAMPLE 4

10 parts of the water-soluble soybean hemicellulose (ii) was dissolved in 45 parts of water, and the solution was adjusted to pH 4.0 with citric acid to form a water phase. Separately, 7 parts of a refined coconut oil, 6.4 parts of SAIB (sucrose acetic isobutyric ester), 1.0 part of dammar, 0.4 part of β-carotin, and 0.2 part of sorbitan monostearate were mixed together to prepare an oil phase. The oil phase was added to the above water phase, and the mixture was subjected to preemulsification with a homomixer. Then, 30 parts of glycerin was added to and homogeneously mixed with the preemulsified product, and the mixture was emulsified with a high-pressure homogenizer (300 kgf/cm$^2$). In the emulsified product, the emulsion remained stable and was stable even after cold storage for 3 months.

Then, 120 parts of granulated sugar and 2 parts of citric acid were dissolved in 880 parts of water, and 1 part of the above-described emulsified product was added thereto to provide a suspension soft drink. This drink was very stable even after the elapse of 3 months.

EXAMPLE 5

3.6 parts of sugar, 3 parts of common salt, 0.3 part of sodium L-glutamate, and 10 parts of the water-soluble soybean hemicellulose (i) were added and completely dissolved in 40 parts of water and 18 parts of vinegar produced by brewing. 15 parts of a salad oil was gradually added thereto, and the mixture was preemulsified with a homomixer and then emulsified with a homogenizer (400 kgf/cm$^2$) to provide an emulsion-dressing-like substance having a low viscosity.

Comparative Example 5

An emulsion dressing was prepared on an experimental basis in the same manner as that of Example 4, except that 0.4% of xanthan gum was used instead of the water-soluble soybean hemicellulose (i) and the reduction of the volume was compensated for by water. The dressing had a very high viscosity.

EXAMPLE 6

5 parts of the water-soluble soybean hemicellulose (iii) was dissolved in 75 parts of water. 20 parts of a refined coconut oil containing 0.1 part of a commercially available milk flavor (Milk FT-013 manufactured by Takasago International Corp.) was added at 70° C. to the solution, and the mixture was premixed with a homomixer. Then, the preemulsified product was emulsified with a high-pressure homogenizer (500 kgf/cm$^2$) to provide a whitener for coffee. The whitener remained stable in an emulsion form even after storage for one month. When the whitener was added to coffee (80° C., pH 5.3) with 5% of sugar, coffee having a mild flavor could be provided without feathering.

EXAMPLE 7

4 parts of the water-soluble soybean hemicellulose (i) and 2 parts of commercially available casein sodium were dissolved in 75 parts of water. 20 parts of a refined coconut oil containing 0.1 part of a commercially available milk flavor (Milk FT-013 manufactured by Takasago International Corp.) was added at 70° C. to the solution, and the mixture was premixed with a homomixer. Then, the preemulsified product was emulsified with a high-pressure homogenizer (500 kgf/cm$^2$) to provide a whitener for coffee. The whitener had an average particle diameter of 0.5 μm. It remained stable in an emulsion form even after storage for one month. The whitener was added to coffee (adjusted to pH 6.8 with sodium hydrogencarbonate) with 8% of sugar, and the coffee was then sterilized at 121° C. for 15 min and stored at 60° C. for 3 months. As a result, it remained stable in a suspension form.

EXAMPLE 8

A sugar solution prepared by dissolving 15 parts of granulated sugar in 15 parts of water and an oil phase prepared by dissolving 1 part of a condensed ricinoleic ester of polyglycerin in 20 parts of an orange oil were emulsified with a homogenizer to provide a water-in-oil emulsion. A solution prepared by dissolving 50 parts of the water-soluble soybean hemicellulose (ii) in 450 parts of water and adjusting the solution to pH 4.0 with citric acid and the whole quantity of the above-described water-in-oil emulsion were preemulsified with a homomixer and then emulsified and mixed together with a homogenizer to provide a water-in-oil-in-water emulsion. The specific gravity of the water-in-oil emulsion of the internal phase of the emulsion was 1.036.

Then, 120 parts of granulated sugar and 2 parts of citric acid were dissolved in 880 parts of water, and 1 part of the above-described emulsion was added to the solution to provide a soft drink. The soft drink remained stable even after the elapse of 3 months.

EXAMPLE 9

6 parts of the water-soluble soybean hemicellulose (iii) was dissolved in 60 parts of water, and 10 parts of propylene glycol, 0.5 part of triethanolamine, 0.5 part of an oleaginous flavor, and a suitable amount of a preservative were added thereto to form a water phase. Separately, 5 parts of stearic acid, 2 parts of beeswax, 5 parts of cetanol, 10 parts of squalane, and 1 part of lanolin were mixed with one another to form an oil phase. The oil phase was added to the above waterphase, and the mixture was preemulsified with a homomixer. Then, the preemulsified product was emulsified with a nanomizer (750 kgf/cm$^2$). The resultant emulsion remained stable even after storage for 6 months. The emulsion was applied as a hand cream to the hand. As a result, good refreshed feeling could be obtained, and the hand remained moist for a long period of time.

EXAMPLE 10

10 parts of the water-soluble soybean hemicellulose (iii) was dissolved in 70 parts of water to provide a water phase, and 20 parts of o,o-dimethyl-o-(3-methyl-4-nitrophenyl) phosphoro-thioate as an insecticide ingredient was added thereto. The mixture was preemulsified with a homomixer and then emulsified with a homogenizer (300 kgf/cm$^2$). The resultant emulsion had an average particle diameter of 0.6 μm and remained stable even after storage at 40° C. for 6 months. Further, decomposition of the active ingredient hardly occurred. The emulsion was diluted to an active ingredient concentration of 250 ppm and applied to completely unfolded leaves of an eggplant, and an insecticidal test was effected using ladybird. As a result, the persistence of the potency was good, and satisfactory results could be obtained.

EXAMPLE 11

10 parts of o-ethyl-o-(3-methyl-6-nitrophenyl)-N-sec-butylphosphothioamidate as a herbicide ingredient was added to 40 parts of a 10 wt % aqueous solution of the water-soluble soybean hemicellulose (i), and the mixture was emulsified at 10000 rpm with a homomixer. Further, 50 g of a 0.8% aqueous solution of Rheogic 250H (manufactured by Nihon Junyaku Co., Ltd.) was added thereto, and the mixture was gently stirred. The resultant emulsion had an average particle diameter of 2.8 μm, remained stable in an emulsion form, and remained stable even after storage for 6 months. Further, decomposition of the active ingredient hardly occurred. The emulsion was diluted and subjected to examination of herbicidal effect after soil treatment. As a result, satisfactory results could be obtained.

EXAMPLE 12

10 parts of the water-soluble soybean hemicellulose (i) was dissolved in 80 parts of water, and 10 parts of an orange oil (manufactured by Yamakatsura Sangyo Co., Ltd.) was dispersed in the solution to bring the volume of the solution to 100 parts. The dispersion was emulsified with a homogenizer (200 kgf/cm$^2$). The resultant emulsion remained stable in an emulsion form without addition of any emulsifier. Thereafter, the emulsion was spray-dried to prepare a powder flavor. The dried powder was observed under a scanning electron microscope and found to be in the form of a microcapsule.

EXAMPLE 13

A powder flavor was prepared on an experimental basis in the same manner as that of Example 12, except that the water-soluble soybean hemicellulose (ii) was used instead of the water-soluble soybean hemicellulose (i). As a result, the emulsifying property and the film-forming property were very good.

EXAMPLE 14

A powder flavor was prepared on an experimental basis in the same manner as that of Example 12, except that the water-soluble soybean hemicellulose (iii) was used instead of the water-soluble soybean hemicellulose (i). AS a result, the emulsifying property and the film-forming property were very good.

Comparative Example 6

A powder flavor was prepared on an experimental basis in the same manner as that of Example 12, except that gum arabic was used instead of the water-soluble soybean hemicellulose (i). As a result, the emulsifying property and the film-forming property were good but inferior to those of the water-soluble soybean hemicellulose (i).

Comparative Example 7

A powder flavor was prepared in the same manner as that of Example 12, except that dextrin (Pinedex manufacturedby Matsutani Kagaku Kogyo Co., Ltd.) was used instead of the water-soluble soybean hemicellulose (i). As a result, the emulsifying property was so poor that no good microcapsule could be prepared.

Comparative Example 8

A powder flavor was prepared in the same manner as that of Example 12, except that a chemically modified starch (Capsul manufactured by Oji-National Co., Ltd.) was used instead of the water-soluble soybean hemicellulose (i). As a result, the emulsifying property was good. However, the film-forming property and odor were poor, and the oxidation resistance was also poor.

The powder flavors prepared in the above-described examples and comparative examples were stored at 40° C. for 20 days to compare the oxidation of the encapsulated material and odor. The results are given in the following table.

| | Items | | | | |
|---|---|---|---|---|---|
| Ex. and Comp. Ex. | Emulsifying property | Film-forming property | Oxidation | Odor | Remarks |
| Ex. 12 | ⊚ | ⊚ | 1.2 | ⊚ | |
| Ex. 13 | ⊚ | ⊚ | 1.3 | ⊚ | |
| Ex. 14 | ⊚ | ⊚ | 1.1 | ⊚ | |
| Comp. Ex. 6 | ○ | ○ | 1.3 | ⊚ | |
| Comp. Ex. 7 | X | X | | | Impossible to encapsulate |
| Comp. Ex. 8 | ○ | Δ | 4.2 | Δ | |

⊚: very good, v: good, Δ: somewhat poor, X: poor
Note)
The oxidation was evaluated in terms of limonene epoxide (mg/g LIMONENE) which is a measure of oxidation of terpenes.

Thus, powder flavors excellent in emulsifying property, film-forming property, oxidation resistance, and odor retention could be provided by using water-soluble soybean hemicelluloses.

EXAMPLE 15

10 parts of the water-soluble soybean hemicellulose (i) was dissolved in 80 parts of water, and 10 parts of a soybean oil (manufactured by Fuji Oil Co., Ltd.) was dispersed in the solution to bring the volume of the solution to 100 parts. The dispersion was emulsified with a homogenizer (200 kgf/cm$^2$). The resultant emulsion remained stable without addition of any emulsifier. Thereafter, the emulsion was spray-dried to prepare a powder fat and oil. The dried powder was observed under a scanning electron microscope and found to be in the form of a good microcapsule.

EXAMPLE 16

A powder fat and oil was prepared on an experimental basis in the same manner as that of Example 15, except that the water-soluble soybean hemicellulose (ii) was used instead of the water-soluble soybean hemicellulose (i). As a result, the emulsifying property and the film-forming property were very good.

EXAMPLE 17

A powder fat and oil was prepared on an experimental basis in the same manner as that of Example 15, except that the water-soluble soybean hemicellulose (iii) was used instead of the water-soluble soybean hemicellulose (i). As a result, the emulsifying property and the film-forming property were very good.

Comparative Example 9

A powder fat and oil was prepared on an experimental basis in the same manner as that of Example 15, except that gum arabic was used instead of the water-soluble soybean hemicellulose (i). As a result, the emulsifying property and the film-forming property were good but inferior to those of the water-soluble soybean hemicellulose (i).

Comparative Example 10

A powder fat and oil was prepared in the same manner as that of Example 15, except that dextrin (Pinedex manufactured by Matsutani Kagaku Kogyo Co., Ltd.) was used instead of the water-soluble soybean hemicellulose (i). As a result, the emulsifying property was so poor that no good microcapsule could be prepared.

Comparative Example 11

A powder fat and oil was prepared in the same manner as that of Example 15, except that a chemically modified starch (Capsul manufactured by Oji-National Co., Ltd.) was used instead of the water-soluble soybean hemicellulose (i). As a result, the emulsifying property was good. However, the film-forming property and odor were poor, and the gas barrier property was also poor.

The powder fat and oil prepared in the above-described examples and comparative examples were stored at 30° C. for 10 days to compare the degree of oxidation of the encapsulated material. The results are given in the following table.

| Ex. and Comp. Ex. | Emulsifying property | Film-forming property | POV | Remarks |
| --- | --- | --- | --- | --- |
| Ex. 15 | ⊚ | ⊚ | 5.2 | |
| Ex. 16 | ⊚ | ⊚ | 3.8 | |
| Ex. 17 | ⊚ | ⊚ | 6.2 | |
| Comp. Ex. 9 | ○ | ○ | 9.6 | |
| Comp. Ex. 10 | X | X | | Impossible to encapsulate |
| Comp. Ex. 11 | ○ | Δ | 22.0 | |

⊚: very good, v: good, Δ: somewhat poor, X: poor
Note)
POV: peroxide value (meq/kg)

Thus, powder fats and oils excellent in emulsifying property, film-forming property, and oxidation resistance could be provided by using water-soluble soybean hemicelluloses.

EXAMPLE 18

10 parts of the water-soluble soybean hemicellulose (i) was dissolved in 80 parts of water, and a mixed oil comprising 6.5 parts of SAIB (sucrose acetic isobutyric ester) and 3.5 parts of an orange oil was dispersed in the solution to bring the volume of the solution to 100 parts. The dispersion was emulsified with a homogenizer. The resultant emulsion was heated to 40° C. and mixed with a gelatin solution separately prepared by dissolving 10 parts of gelatin in 80 parts of warm water of 40° C. Further, 500 parts of hot water of 40° C. was added thereto to dilute the mixed colloidal solution comprising a water-soluble hemicellulose and gelatin, and the pH value of the mixed colloidal solution was adjusted to 4.2 with a 10% acetic acid solution to form a coacervate. After the coacervate was formed, the system was cooled to 5° C. to prepare a microcapsule. After the microcapsule was formed, the supernatant was filtered off, washed with cold water, suspended in cold water, and spray-dried to provide an microcapsule flavor of an orange oil. Then, 120 parts of granulated sugar was dissolved in 880 parts of water, and the solution was adjusted to pH 3.0 with a 50% citric acid solution. Subsequently, 0.2 part of the above-described microcapsule flavor was added thereto to provide an orange-like soft drink. The soft drink was quite stable even after the elapse of 3 months. Further, the microcapsule flavor remained stable even after cold storage for 3 months.

EXAMPLE 19

A microcapsule flavor was prepared on an experimental basis in the same manner as that of Example 18, except that the water-soluble soybean hemicellulose (ii) was used instead of the water-soluble soybean hemicellulose (i). The microcapsule flavor was stable. Further, an orange-like soft drink prepared using this flavor was also stable.

EXAMPLE 20

A microcapsule flavor was prepared on an experimental basis in the same manner as that of Example 18, except that the water-soluble soybean hemicellulose (iii) was used instead of the water-soluble soybean hemicellulose (i). The microcapsule flavor was stable. Further, an orange-like soft drink prepared using this flavor was also stable. The microcapsule flavor compared favorably with a control microcapsule flavor prepared using gum arabic instead of the water-soluble soybean hemicellulose (i).

Comparative Example 12

A microcapsule flavor was prepared in the same manner as that of Example 18, except that a solution of 1 part of sodium alginate in 89 parts of water was used instead of the water-soluble soybean hemicellulose (i). An orange-like soft drink was prepared using the microcapsule flavor. As a result, the flavor was immediately separated, suggesting that the preparation of the microcapsule was unsuccessful.

The microcapsule flavors and orange-like soft drinks prepared in the above-described examples and comparative examples were stored at 5° C. for 90 days, and the state of these products was observed. The results are given in the following table.

| Ex. and Comp. Ex. | Encapsulated flavor | | Orange-like soft drink | |
|---|---|---|---|---|
| | State | Average particle diameter (μm) | State | Odor |
| Ex. 18 | ⊚ | 25.6 | ⊚ | ○ |
| Ex. 19 | ⊚ | 34.2 | ○ | ⊚ |
| Ex. 20 | ⊚ | 21.3 | ⊚ | ○ |
| Control | ⊚ | 35.1 | ⊚ | ○ |
| Comp. Ex. 12 | X | 124.6 | X | ○ |

⊚: very good, v: good, Δ: somewhat poor, X: poor

Note)
The average particle diameter was measured with a laser diffraction particle size distribution measuring device (LA-500 manufactured by Horiba Ltd.).

As is apparent from the above table, when use was made of water-soluble soybean hemicelluloses, the resultant microcapsule flavors had a good stability and were stable also when used in drinks.

EXAMPLE 21

5 parts of the water-soluble soybean hemicellulose (i) and 5 parts of gelatin were dissolved in 90 parts of warm water of 40° C. 20 parts of a mixed paste comprising a ground sardine and rice starch was added and suspended therein with stirring. Further, 200 parts of hot water of 40° C. was added thereto to dilute the mixed colloidal solution, and the pH value of the mixed colloidal solution was adjusted to 4.2 with a 10% acetic acid solution to form a coacervate. After the coacervate was formed, the system was cooled to 5° C. to prepare a microcapsule. After the microcapsule was prepared, 2 parts of sodium alginate was added and completely dissolved therein. After the sodium alginate was dissolved, the microcapsule was added dropwise to a 0.1% calcium chlorcalcium chloride solution while suspending by stirring to effect double coating. After the completion of the double coating, the microcapsule was washed with water, dehydrated by filtration, and subjected to circulation drying at 50° C. to prepare a microcapsule feed. 10 goldfish were fed with the microcapsule feed to determine the survival rate. For comparison, 10 goldfish were fed with a commercially available feed (Angel Color Enhancer manufacturedby Nippon Pet Food Co., Ltd.) in the same amount as that in Example 21.

The goldfish were fed with the feed of Example 21 and the control feed for 90 days. The results are given in the following table in comparison with one another.

| | Ex. 21 | | Control | |
|---|---|---|---|---|
| | Number of survivals | Survival rate (%) | Number of survivals | Survival rate (%) |
| 1 day after initiation of feeding | 10 | 100 | 10 | 100 |
| 7 days after initiation of feeding | 10 | 100 | 10 | 100 |
| 30 days after initiation of feeding | 10 | 100 | 10 | 100 |
| 90 days after initiation of feeding | 9 | 90 | 10 | 100 |

Thus, good microcapsule feeds could be prepared by using water-soluble soybean hemicelluloses.

EXAMPLE 22

20 parts of gelatin was dissolved in 200 parts of warm water of 50° C. A solution prepared by dissolving 1.5% of crystal violet lactone and 1.0% of benzoyl leuco methylene blue in 200 ml of a mixed solvent comprising an alkylnaphthalene and kerosine in a mixing ratio of 9:1 was added to the resultant colloidal solution, and the mixture was emulsified with a homogenizer. A solution of 20 parts of the water-soluble hemicellulose (i) dissolved in 200 parts of warm water of 50° C. was added thereto, and they were mixed together with stirring. Further, 1000 parts of warm water of 50° C. was added to dilute the solution. Thereafter, the solution was adjusted to pH 4.2 with a 10% acetic acid solution to form a coacervate. After the formation of the coacervate, the system was cooled to 5° C., 5 ml of a 25% glutaraldehyde solution was added thereto, and the mixture was stirred for 1 hr. Thereafter, the solution temperature was raised to 30° C., and a curing treatment was effected at 30° C. for 12 hr to prepare a microcapsule for pressure-sensitive copying paper.

The microcapsule thus obtained was coated at a coverage of 5 g/m$^2$. A colorant prepared by dispersing 100 parts of a zinc salt of 5-phenylsalicylic acid and 30 parts of a styrene/butadiene latex (solid content: 50%) in 200 parts of water was coated on other paper at a coverage of 5 g/m$^2$. The papers were superposed, and the laminate was pressed with a pencil. As a result, a clear color development was observed on the pressed portion.

EXAMPLE 23

10 parts of the water-soluble soybean hemicellulose (i) and 10 parts of gelatin were dissolved in 180 parts of warm water of 40° C. to prepare a mixed colloidal solution. 10 parts of an orange oil was dispersed in the colloidal solution, and the mixture was emulsified with a homogenizer. Further, 500 parts of warm water of 40° C. was added to the emulsion with the emulsion kept at 40° C. to dilute the emulsion. The diluted emulsion was adjusted to pH 4.2 with a 10% acetic acid solution to form a coacervate. After the formation of the coacervate, the system was cooled to 5° C., 1 ml of a 37% formaldehyde solution was added thereto, and the mixture was stirred for 1 hr. Thereafter, the solution was adjusted to pH 9 by addition of 2N sodium hydroxide. Then, the solution temperature was raised to 50° C., and a curing treatment was effected for 5 hr. After the completion of the curing treatment, the supernatant was discarded, and the total quantity was brought to 100 parts by a solution of 10 parts of Nikaresin 305 (manufactured by Nippon Carbide Industries Co., Ltd.) dissolved in 300 parts of water. The mixture was adjusted to pH 5.0 with 10% hydrochloric acid while stirring and stirred at 20° C. for 10 hr. The resultant microcapsule flavor was washed with water, filtered, and subjected to circulation drying at 80° C.

The microcapsule flavor prepared in Example 23 was coated on paper, and the coated paper was rubbed with a finger. As a result, a flavor of an orange was successfully emitted. This flavor was successfully maintained even after the elapse of 90 days and emitted by rubbing the coated paper with a finger.

EXAMPLE 24

10 parts of the water-soluble soybean hemicellulose (iii) and 10 parts of gelatin were dissolved in 180 parts of warm water of 40° C. to prepare a mixed colloidal solution. 20 parts of o,o-dimethyl-o-(3-methyl-4-nitrophenyl) phosphorothioate as an insecticide ingredient was added thereto, and the mixture was emulsified with a homogenizer. Further, 500 parts of warm water of 40° C. was added to the emulsion with the emulsion kept at 40° C. to dilute the emulsion. The diluted emulsion was adjusted to pH 4.2 with a 10% acetic acid solution to form a coacervate. After the formation of the coacervate, the system was cooled to 5° C., 1 ml of a 37% formaldehyde solution was added thereto, and the mixture was stirred for 1 hr. Thereafter, the solution was adjusted to pH 9 by addition of 2N sodium hydroxide. Then, the solution temperature was raised to 50° C., and a curing treatment was effected for 12 hr. After the completion of the curing treatment, a solution of 30 parts of cellulose acetate phthalate in 700 parts of an aqueous alkaline solution (pH 9) was added thereto, and the mixture was adjusted to pH 5.0 by addition of 10% hydrochloric acid with stirring and then stirred at 20° C. for additional 1 hr. The microcapsule insecticide was washed with water, filtered, and subjected to circulation drying at 50° C. The microcapsule insecticide was diluted to an active ingredient concentration of 250 ppm and applied to completely unfolded leaves of an eggplant, and an insecticidal test was effected using ladybird. As a result, the persistence of the potency was good, and satisfactory results could be obtained.

EXAMPLE 25

2 parts of o-ethyl-o-(3-methyl-6-nitrophenyl)-N-sec-butylphosphothioamidate as a herbicide ingredient was added to a mixed colloidal solution prepared by dissolving 5 parts of the water-soluble soybean hemicellulose (iv) and 10 parts of gelatin in 180 parts of warm water of 50° C., and the mixture was emulsified at 10000 rpm with a homomixer. Further, 50 parts of a 0.8% aqueous solution of Rheogic 250H (manufactured by Nihon Junyaku Co., Ltd.) was added thereto, and the mixture was emulsified with a homogenizer. Further, 500 parts of warm water of 40° C. was added to the emulsion with the emulsion kept at 40° C. to dilute the emulsion. The diluted emulsion was adjusted to pH 4.2 with a 10% acetic acid solution to form a coacervate. After the formation of the coacervate, the system was cooled to 5° C., 5 ml of a 25% formaldehyde solution was added thereto, and the mixture was stirred for 1 hr. Thereafter, the solution temperature was raised to 30° C., and a curing treatment was effected for 5 hr. After the completion of the curing treatment, a solution of 30 parts of benzylaminomethyl cellulose in 700 parts of an aqueous acidic solution (pH 4) was added thereto, and the mixture was adjusted to pH 10.0 by addition of 10% sodium hydroxide with stirring and then stirred at 20° C. for 12 hr. The microcapsule insecticide was washed with water, filtered, and subjected to circulation drying at 50° C. Decomposition of the active ingredient hardly occurred. Further, the microcapsule insecticide was applied to soil to examine the herbicidal effect. The results were satisfactory.

As described above, when an emulsion flavor is prepared on an experimental basis by using the emulsifier of the present invention, the emulsion can remain stable for a long period of time also in drinks as a final product. Further, use thereof for preparing dressings can provide very fluid emulsion dressings as opposed to use of xanthan gum. Further, the emulsifier of the present invention has made it possible to prepare creams less susceptible to a change of pH. Further, it has been found that the emulsifier of the present invention can be effectively utilized for emulsification of cosmetics, drugs, agricultural chemicals, various oil solutions for industrial application and the like. When a water-soluble hemicellulose derived from a soybean cotyledon was used as a base for powdering, it exhibited excellent emulsifying property, film-forming property, and oxidation resistance. This effect compares favorably with that attained by gum arabic which exhibits the best effect when used as a base for powdering. Further, in the emulsifier of the present invention, since beans, i.e., an agricultural product which can be stably applied, are used as the raw material, there is no fear of the price being subjected to a sharp fluctuation. Further, the water-soluble hemicellulose derived from a soybean cotyledon used in the present invention can be produced in a relatively simple manner, so that it is considered that the production cost is also considerably low. Further, use of the water-soluble hemicellulose enables a coacervate comparable favorably with gum arabic and a microcapsule to be prepared by complex coacervation, which renders the present invention useful for use in the preparation of foods such as edible flavors, artificial feeds, industrial products, such as pressure-sensitive copying paper and flavors for printing, and agricultural chemicals, such as insecticides and herbicides.

We claim:

1. An emulsifier comprising as an active ingredient a water-soluble hemicellulose obtained by heat-degradation of a soybean cotyledon in an acidic region followed by extraction, the water-soluble hemicellulose having a molecular weight from 5,000 to 1,000,000.

2. An emulsifier according to claim 1, wherein said water-soluble hemicellulose in a 10% aqueous solution has a viscosity no greater than 200 cP.

3. An emulsion composition comprising an emulsifier according to claim 1.

4. An emulsion composition according to claim 3, which has an oil phase of which the specific gravity has been adjusted with a specific gravity adjustor having a specific gravity of 1 or more.

5. An emulsion composition according to claim 3, which is in the form of a coacervation.

6. A powder composition produced by powdering an emulsion composition according to claim 3.

7. A powder composition according to claim 6, which is in the form of a microcapsule.

8. An emulsion composition according to claim 4, which is in the form of a coacervation.

* * * * *